(12) United States Patent
Susen et al.

(10) Patent No.: US 10,478,475 B2
(45) Date of Patent: Nov. 19, 2019

(54) USE OF VON WILLEBRAND FACTOR

(71) Applicants: Laboratoire Francais du Fractionnement et des Biotechnologies, Les Ulis (FR); CTRE Hospitalier Universitaire de Lille, Lille (FR); Universite Lille 2 Droit et Sante, Lille (FR)

(72) Inventors: Sophie Susen, Lille (FR); Andre Vincentelli, Lille (FR); Eric Van Belle, Marcq en Baroeul (FR); Antoine Rauch, Lille (FR); Flavien Vincent, Lille (FR)

(73) Assignees: LABORATOIRE FRANCAIS DU FRACTIONNEMENT ET DES BIOTECHNOLOGIES, Les Ulis (FR); CTRE HOSPITALIER UNIVERSITAIRE DE LILLE, Lille (FR); UNIVERSITE LILLE 2 DROIT ET SANTE, Lille (FR)

( * ) Notice: Subject to any disclaimer, the term of this patent is extended or adjusted under 35 U.S.C. 154(b) by 0 days.

(21) Appl. No.: 15/564,783

(22) PCT Filed: Apr. 6, 2016

(86) PCT No.: PCT/EP2016/057494
§ 371 (c)(1),
(2) Date: Oct. 6, 2017

(87) PCT Pub. No.: WO2016/162369
PCT Pub. Date: Oct. 13, 2016

(65) Prior Publication Data
US 2018/0110838 A1 Apr. 26, 2018

(30) Foreign Application Priority Data

Apr. 7, 2015 (FR) ..................... 15 52982

(51) Int. Cl.
| A61K 38/36 | (2006.01) |
| A61K 38/37 | (2006.01) |
| A61K 9/00 | (2006.01) |
| A61P 7/04 | (2006.01) |
| A61K 47/42 | (2017.01) |
| A61K 9/19 | (2006.01) |

(52) U.S. Cl.
CPC ............ *A61K 38/36* (2013.01); *A61K 9/0019* (2013.01); *A61K 38/37* (2013.01); *A61P 7/04* (2018.01); *A61K 9/19* (2013.01); *A61K 47/42* (2013.01)

(58) Field of Classification Search
None
See application file for complete search history.

(56) References Cited

U.S. PATENT DOCUMENTS 6,518,482 B2 2/2003 Lubon et al.
6,903,069 B2 6/2005 Pingel et al.

FOREIGN PATENT DOCUMENTS

| EP | 0359593 A1 | 3/1990 |
| EP | 0503991 A1 | 9/1992 |
| EP | 0264166 B1 | 8/1996 |
| JP | 2014516088 A | 7/2014 |

OTHER PUBLICATIONS

Public Assessment Report for Willfact 1000 IU, DE/H/1935/001/MR, published Dec. 14, 2010 (Year: 2010).*
European Medicines Agency "What we publish on medicines and when" dowloaded from www.ema.europa.eu/en/medicines/what-we-publish-medicines-when on Dec. 14, 2018 (Year: 2018).*
Cohn et al., "Preparation and Properties of Serum and Plasma Proteins. IV. A Systems for the Separation into Fractions of the Protein and Lippoprotein Components of Biological Tissues and Fluids," J. Am. Chem. Soc., vol. 68, p. 459, Mar. 1946.
Cushing et al., "Factor VIII/von Willebrand factor concentrate therapy for ventricular assist device-associated acquired von Willebrand disease," Transfusion, vol. 52, pp. 1535-1541, Jul. 2012.
Fischer et al., "Von Willebrand factor, a versatile player in gastro-intestinal bleeding in left ventricular assist device recepients," Transfusion, vol. 55, No. 1, pp. 51-54, Jul. 2014.
Geisen et al., Non-surgical bleeding in patients with ventricular assist devices could be explained by acquired von Wiliebrand disease, European Journal of Cardio-Thoracic Surgery, vol. 33, No. 4, pp. 679-684, Feb. 2008.
Gorlinger et al,, "Coagulation management in patients undergoing mechanical circulatory support," Bailliere's Best Practice and Research, Clincial Anesthesiology, vol. 26, No. 2, pp. 179-198, Jun. 2012.
International Search Report for International Application No. PCT/EP2016/057494 dated Jul. 1, 2016.
Kistler et al., "Large Scale Production of Human Plasma Fractions," Vox Sang, vol. 7, pp. 414-424, 1962.
Stone et al., "Current management of von Willebrand disease and von Willebrand syndrome," Current Opinion in Anaesthesiology, vol. 27, No. 3, pp. 353-358, Jun. 2014.

* cited by examiner

*Primary Examiner* — Christina Bradley
(74) *Attorney, Agent, or Firm* — Potomac Law Group, PLLC

(57) ABSTRACT

The present invention relates to a von Willebrand factor composition for the prevention and/or the treatment of haemorrhage and/or bleeding in patients with mechanical circulatory support.

12 Claims, No Drawings

USE OF VON WILLEBRAND FACTOR

The present invention relates to a novel use of von Willebrand factor, and in particular to the treatment and/or the prevention of haemorrhage and/or bleeding in patients with mechanical circulatory support.

Mechanical circulatory support is an intracorporeal or extracorporeal device capable of replacing, either totally or partially, the circulatory functions normally performed by the heart. Its objective is to maintain or restore the main functions of the organism, and in particular to ensure, as the case may be, a uni- or biventricular discharge or to completely take over the function of the failing heart. This type of device is prescribed when the patient's haemodynamic status requires it, in particular in three specific indications:
- in patients waiting for a heart transplant in order to avoid a deterioration in the haemodynamic status of the patient due to a prolonged wait on the transplant list;
- in patients awaiting recovery, in particular in patients having suffered viral myocarditis, a drug overdose or having a low cardiac output after heart surgery under extracorporeal circulation;
- in patients who would possibly be candidates for a heart transplant but who unfortunately present a contraindication for such a surgical intervention (pulmonary hypertension, neoplasia in remission but not cured, age).

The first circulatory support systems were all of the pneumatic type. They were all composed of a rigid outer shell inside which there is either a bag or a diaphragm made of polyurethane. Mechanical or biological valves ensured a unidirectional flow. They were connected to a drive console which was generally very large and cumbersome, restricting the movements the patient could make. Compressed air came from a wall socket at the hospital (CardioWest®) with the possibility of operating temporarily with bottles of compressed air situated inside the console. All of the other systems were connected to consoles inside which air was compressed by a compressor. The operating principle of these devices is simple: a low pressure around the bag or under the diaphragm ensures that the prosthesis is filled. In reverse, during the ejection phase, compressed air compresses the bag or pushes back the diaphragm, thus making possible the rhythmic ejection of the blood. All of these ventricles therefore provide a pulsed flow. Among these pneumatic ventricles there are those that are paracorporeal which can be used for univentricular support (most often on the left) or biventricular support, and implanted ventricles (Total Artificial Heart from CardioWest®). All of these ventricles provide an excellent haemodynamic performance and can be used over long periods making it possible to wait for a transplant under the best possible conditions. The system used most often is, without doubt, the Thoratec® system which has a novel drive console (TLC-II) which improves the patient's comfort and also allows the patient to leave hospital and to return home.

Ventricles of the last generation operate with electrical energy. In the 1980s and 1990s there were two electromechanical ventricles implanted between the top of the left ventricle and the ascending thoracic aorta (Novacor®, HeartMate XVE®). The pump was implanted behind the muscles of the abdominal wall and an electric cable connected this pump to a controller and to a power source. The flow delivered was of the pulsed type. The Novacor® is no longer available and the HeartMate® is hardly used any more, at least in Europe.

The last generation of implantable pumps is of the rotary type. These implantable pumps can be classified in two groups:
- centrifugal pumps such as DuraHeart® or HeartWare® and,
- axial pumps such as HeartMate II®, MicroMed DeBakey®, BerlinHeart Incor® or Jarvik 2000®.

These pumps delivering a continuous, not a pulsed, flow do not need valves to ensure a unidirectional flow. In the case of most of these rotary pumps, the rotor turns about a shaft.

However, it has been found that patients with this type of implantable pump, delivering a continuous, not a pulsed, flow develop an acquired von Willebrand disease. In fact, in these patients, a significant fall in the fraction of high-molecular weight multimers of von Willebrand factor has been found, thus causing mainly gastro-intestinal bleeding, which doctors have difficulty treating.

Fisher et al. (Transfusion, 2015; vol. 55(1), pp. 51-54.) reports the case of a patient with mechanical circulatory support using a continuous flow pump (HeartMate II), repeatedly suffering severe gastro-intestinal bleeding following the implantation of the pump. After the failure of conventional treatments, this patient received 80 IU/kg of body weight of von Willebrand factor on day 17, 18 and 19 after the introduction of the mechanical circulatory support. The treatment with von Willebrand factor was maintained and a new dose of 80 IU/kg of body weight was again administered to the patient on days 21, 23, 27 and 30 after the operation. However, on day 41, the doctors found that the patient's ileum appeared hyperdense, suggesting active haemorrhage in this region. A new administration of von Willebrand factor was then carried out every two days from day 41 to day 53 after the operation. On day 57 after the operation, the doctors discovered three angiodysplasic lesions in the duodenum, lesions likely to cause serious haemorrhage. As a result, therefore, despite a massive administration of von Willebrand factor on days 17 to 19 after the operation, the doctors could not stop the occurrence of a new gastro-intestinal (ileum) haemorrhage.

Cushing et al. (Transfusion, 2012; vol. 52, pp. 1535-1541) report the case of a patient with mechanical circulatory support using a continuous flow pump (HeartMate II) while waiting for a heart transplant. The patient developed a haemorrhage in the duodenal bulb 9 days after the introduction of the mechanical circulatory support device. This haemorrhage was treated with a blood transfusion and the administration of aminocaproic acid. 47 days after the intervention, the patient had seepage in the gastric area and in the duodenal bulb as well as active bleeding at the duodenojejunal junction. On the $49^{th}$ day after the placement of the mechanical circulatory support device, the patient received a dose of 60 IU/kg of body weight of a pharmaceutical composition comprising von Willebrand factor and factor VIII every eight hours, in three doses while continuing the administration of aminocaproic acid. Treatment with the composition of von Willebrand factor and factor VIII was continued for 33 days with decreasing doses. However, the patient developed bruises around the left eye and a thrombus at the pump a few days later, resulting in cessation of the treatment. The authors concluded that the treatment with the composition of von Willebrand factor and factor VIII made it possible to treat gastro-intestinal haemorrhage and/or bleeding, but that this treatment requires very close monitoring of thromboses in the pump circuit, in particular because of the presence of factor VIII in the therapeutic concentrate. As a result, therefore, although it was possible to treat haemorrhages in the patient being studied with an administration of the composition of von Willebrand factor and factor VIII, the administration of this product can lead to the occurrence of thrombosis.

Consequently, it would appear necessary to provide a method for the prevention and/or a method for the treatment of haemorrhage and/or bleeding which could be applied to patients with mechanical circulatory support, in order to prevent the occurrence of these haemorrhages and/or of this bleeding, without the fear of causing an additional thrombosis and without the fear of a possible relapse, i.e. without the fear of developing new haemorrhages or new bleeding.

The inventors have shown, surprisingly, that the administration of a pharmaceutical composition comprising von Willebrand factor at a fixed dose and under specific conditions made it possible to prevent the risks associated with the introduction of mechanical circulatory support. More particularly, the inventors have shown that this preventative administration of von Willebrand factor made it possible, surprisingly, to reduce by more than 60% the risks associated with the introduction of mechanical circulatory support, namely to reduce by more than 60% the occurrence of haemorrhage and/or bleeding in these patients. This preventative administration of von Willebrand factor preferably makes it possible to reduce the occurrence of haemorrhage and/or bleeding in these patients by more than 70%, preferably 80%, preferably 90%. Advantageously, this administration of von Willebrand factor makes it possible to permanently eliminate any risk of haemorrhage and/or bleeding in patients with mechanical circulatory support, including the risks of relapse.

In another advantageous embodiment, the administration of a pharmaceutical composition comprising von Willebrand factor according to the invention makes it possible to reduce the frequency of clinically significant bleeding in comparison with usual care.

The invention therefore relates to a pharmaceutical composition comprising von Willebrand factor intended to be used in the prevention of haemorrhage and/or bleeding in patients with mechanical circulatory support.

The term "bleeding" means an (internal or external) blood flow outside the natural blood circulation of low quantity. When the loss of blood is significant and likely to be life-threatening it is then called "haemorrhage". The bleeding or haemorrhage may be through the skin, through a natural orifice or may be internal. The term "clinically significant bleeding" means an internal or external bleeding leading to death or to a prolonged period in hospital, or requiring re-hospitalization, surgery or the transfusion of at least 3 units of red blood cells, or causing an increase in haemoglobin to a level higher than 3 g/dl, or which is resistant to conventional treatment methods.

Within the meaning of the present invention, by "pharmaceutical composition" is meant a pharmaceutical composition in liquid form, in particular in the form of a solution or a suspension as well as a pharmaceutical composition in powder form. This pharmaceutical composition comprises at least one active ingredient, the von Willebrand factor and pharmaceutically acceptable excipients.

The term "von Willebrand factor" or "vWF" includes the polypeptides comprising the sequence of wild-type human von Willebrand factor or of von Willebrand factor derived from another species (for example bovine, porcine, canine or murine). It also comprises the natural allelic variations of von Willebrand factor which can exist and any form or degree of glycosylation or other post-translational modification. The term "von Willebrand factor" also includes the variants of von Willebrand factor which have the same or a higher biological activity with respect to the activity of the wild form, these variants in particular have at least 70%, preferably 75%, preferably 80%, preferably 85%, preferably 90%, preferably 92%, preferably 94%, preferably 95%, preferably 96%, preferably 97%, preferably 98%, preferably 99%, preferably 100% homology with the nucleotide sequence of wild-type von Willebrand factor. Advantageously, the von Willebrand factor is a human von Willebrand factor.

In an advantageous embodiment, the pharmaceutical composition comprising von Willebrand factor intended to be used in the prevention of haemorrhage and/or bleeding in patients with mechanical circulatory support is depleted of factor VIII. The term "depleted of factor VIII" means that the composition of the invention does not contain factor VIII or that it is present in a negligible quantity. In fact, the inventors found that the elimination of this clotting factor made it possible to reduce the risks of the occurrence of thrombosis, unlike the combined FVIII/vWF pharmaceutical compositions already marketed such as, in particular, the product constituted by 160 IU/ml von Willebrand factor and 66.6 IU/ml factor VIII.

Advantageously, the residual amount of factor VIII in the pharmaceutical composition comprising von Willebrand factor according to the invention is less than or equal to 10 IU/100 IU VWF:RCo. This level is measured using the von Willebrand ristocetin cofactor assay method (VWF:RCo) with respect to the international standard of concentrated von Willebrand factor defined by the World Health Organisation (WHO). The activity of the von Willebrand factor in the composition of the invention is preferably 100 IU for 1 ml of reconstituted solution. The content of residual factor VIII in the composition according to the invention is therefore divided by a minimum of a factor of 4 with respect to the products on the market, thus making it possible to limit the risk of thrombosis by controlling and reducing as far as possible the exogenous supply of FVIII. The residual amount of factor VIII in the pharmaceutical composition comprising von Willebrand factor according to the invention is preferably less than or equal to 10 IU/100 IU VWF:RCo, preferably less than 8 IU/100 IU VWF:RCo, preferably less than 6 IU/100 IU VWF:RCo, preferably less than 4 IU/100 IU VWF:RCo. In a particular embodiment, the composition comprising von Willebrand factor is entirely free from blood clotting factor VIII.

In another embodiment, the pharmaceutical composition comprising von Willebrand factor also comprises factor VIII in a non-negligible quantity. Then, the factor VIII/von Willebrand factor ratio is advantageously between 1/10 and 5/10 IU/ml.

In an advantageous embodiment, the pharmaceutical composition comprising von Willebrand factor intended to be used in the prevention of haemorrhage and/or bleeding in patients with mechanical circulatory support is depleted of ADAMTS13. The term "depleted of ADAMTS13" or "depleted of ADAMTS13 protein" means that the composition of the invention does not contain any ADAMTS13 protein or that this ADAMTS13 protein is present in a negligible quantity or that the ADAMTS13 activity is negligible. In fact, the inventors found that this protein had a tendency to weaken the von Willebrand factor, and even to degrade it, and also that the activity of this protein is increased by the shearing forces induced by the mechanical circulatory support device. Thus, the absence of this protein or its presence in a negligible quantity made it possible to reduce the risks of the occurrence of haemorrhage and/or bleeding in patients with mechanical circulatory support.

Advantageously, the pharmaceutical composition comprising von Willebrand factor is depleted of ADAMTS13.

In another particular embodiment, the residual amount of ADAMTS13 in the pharmaceutical composition comprising von Willebrand factor according to the invention is less than or equal to 0.15 µg/ml. Preferably, the residual amount of ADAMTS13 is less than or equal to 0.10 µg/ml, preferably less than or equal to 0.05 µg/ml, preferably less than or equal to 0.01 µg/ml. The residual amount of ADAMTS13 is preferably between 0.01 µg/ml and 0.15 µg/ml.

Advantageously, the pharmaceutical composition comprising von Willebrand factor does not contain ADAMTS13 activity.

In another particular embodiment, the residual level of ADAMTS13 activity in the pharmaceutical composition comprising von Willebrand factor according to the invention is less than or equal to the detection limit, or less than or equal to 0.03 ADAMTS13:Act [U/ml].

This level is measured using the method described in Kokame et al. (British Journal of Haematology, 2005, vol. 129, pp. 93-100), using FRET (fluorescence resonance energy transfer) and the fluorogenic substrate FRETS-VWF73 (Peptides International, Louisville, USA). The amount of residual ADAMTS13 in the composition according to the invention is at least 2 to 3 times lower with respect to the products on the market which comprise at least 0.13±0.07 ADAMTS13:Act [U/ml], thus making it possible to avoid any risk of the occurrence of haemorrhage and/or bleeding in patients with mechanical circulatory support. In a preferred embodiment, the residual amount of ADAMTS13 in the pharmaceutical composition comprising von Willebrand factor according to the invention is less than 0.10 ADAMTS13:Act [U/ml], preferably less than 0.05 ADAMTS13:Act [U/ml]. In a particular embodiment, the composition comprising von Willebrand factor is entirely free of ADAMTS13. In another embodiment of the invention, the quantity of ADAMTS13 in the composition comprising von Willebrand factor of the invention is adjusted in order to avoid the presence of ultra large multimers (>20 mers). In this case, the ADAMTS13 can advantageously be of plasmatic origin and copurified with the composition comprising von Willebrand factor of the invention, or be of recombinant origin and advantageously be added to the composition comprising von Willebrand factor of the invention of recombinant origin.

The distribution of the multimeric forms of von Willebrand factor is defined after analysis of an electrophoresis gel making it possible to quantify the size of the mers (sub-units) in multiples of the monomer sub-unit of 225 kD. Mers with a size of 225×2 to 225×15 are thus described. By high-molecular weight multimers of the pharmaceutical composition comprising von Willebrand factor is meant multimers starting from 10 monomers.

In a particular embodiment, the content of high-molecular weight multimers in the pharmaceutical composition comprising von Willebrand factor is close to that of plasma.

In another particular embodiment, the content of high-molecular weight multimers in the pharmaceutical composition comprising von Willebrand factor is sufficiently maintained in order to allow sufficient in vivo activity of the pharmaceutical composition.

Advantageously, the pharmaceutical composition comprising von Willebrand factor according to the invention has a content of high-molecular weight multimers of at least 65%, preferably 70%, yet more preferably 75%, particularly preferably 80% of the total multimer content of von Willebrand factor contained in the pharmaceutical composition. The presence of at least 65% of high-molecular weight multimers confers to the composition according to the invention a better therapeutic efficacy.

The pharmaceutical composition according to the invention can comprise in addition one or more excipients, making it possible to stabilize the von Willebrand factor and making it possible to solubilize the lyophilized forms of the von Willebrand factor.

In particular, the excipients can be chosen from:
a hydrophilic amino acid or one bearing a positively-charged side chain,
optionally a hydrophobic amino acid,
a salt,
a protein stabilizer,
or a mixture thereof.

The hydrophilic (or polar) amino acids or the amino acids bearing a positively-charged side chain include lysine, arginine, histidine, glycine, serine, threonine, tyrosine, asparagine and glutamine. Among the hydrophilic amino acids or those bearing a positively-charged side chain, arginine is preferably used, or one of the salts derived therefrom such as arginine hydrochloride or also arginine phosphate. The amino acids such as glycine and/or lysine, or one of the salts derived therefrom such as lysine hydrochloride can advantageously be added. In particular, the hydrophobic amino acids include the following amino acids: alanine, valine, leucine, isoleucine, phenylalanine, tryptophan, proline.

The salt can be an alkali metal salt, an alkaline earth metal salt or a transition metal salt. In particular, sodium citrate, calcium chloride and zinc chloride can be mentioned by way of example as salt. In a preferred manner, the salt used is preferably sodium citrate or calcium chloride.

The protein stabilizer can be chosen from among the known protein stabilizers, for example albumin and factor VIII. Advantageously, the preferred protein stabilizer is albumin, preferably human albumin.

Advantageously, the composition comprises von Willebrand factor as active ingredient and the following pharmaceutically acceptable excipients: albumin, arginine hydrochloride, glycine, sodium citrate and calcium chloride. More particularly, the composition can comprise:
human von Willebrand factor;
albumin, preferably human albumin;
arginine, optionally in the form of the hydrochloride;
glycine;
sodium citrate;
calcium chloride.

Reconstitution from powder in the form of an injectable preparation can be carried out by adding water for injections (WFI water).

The term "prevention" or "prophylaxis" or "preventative treatment" or "prophylactic treatment" comprises a treatment leading to the prevention of a disease as well as a treatment reducing and/or delaying the incidence of a disease or the risk of it occurring. According to the invention, the von Willebrand factor composition is particularly useful for preventing or reducing haemorrhage and/or bleeding associated with the introduction of a mechanical circulatory support device. For the purposes of the present invention, the preventative or prophylactic treatment can take action before the introduction of the mechanical circulatory support device in the patient or after the introduction thereof, i.e. in the days following the introduction of the device, but in any case before the occurrence of bleeding or haemorrhage.

In a preferred embodiment, the pharmaceutical composition comprising von Willebrand factor is administered to the patient with mechanical circulatory support at a dose of at least 30 IU/kg of body weight.

By "administration" is meant the injection into the patient of the pharmaceutical composition according to the invention. This administration comprises parenteral injections, such as in particular intravenous, intramuscular, sub-cutaneous, intraorbital, intradermal, intra-spinal and intraperitoneal injections as well as infusion directly into a tissue or an organ. Administration orally or by using the airways, for example by inhalation, are also envisaged within the scope of the present invention. Particularly advantageously, the pharmaceutical composition comprising von Willebrand factor is administered intravenously.

Advantageously, the pharmaceutical composition comprising von Willebrand factor according to the invention is administered to the patient at a dose of at least 40 IU/kg of body weight, preferably 45 IU/kg of body weight, preferably 50 IU/kg of body weight, preferably 55 IU/kg of body weight, preferably 60 IU/kg of body weight, preferably 65 IU/kg of body weight. Particularly advantageously, the dose is 50 IU/kg of body weight. A person skilled in the art will know how to adapt the dose depending on the administration route chosen. In particular, if intravenous administration is chosen, the dose preferably administered would be 50 IU/kg of body weight.

Advantageously, the dosing regime provides a modification of the multimer distribution of von Willebrand factor with an increase of 20% in the multimers larger than 15 mers for 1 hour after the injection. Advantageously, the dosing regime provides a modification of the multimer distribution of von Willebrand factor with an increase in the multimers larger than 15 mers for at least 30 mins. Preferably, the dosing regime provides a modification of the multimer distribution of von Willebrand factor with an increase in the multimers larger than 15 mers for at least 45 mins. Advantageously, the dosing regime provides a modification of the multimer distribution of von Willebrand factor with an increase in the multimers larger than 15 mers for at least 1 hour after the injection. This temporary increase and this modification make it possible to re-establish a normal angiogenesis in the microcirculation.

Advantageously, the dosing regime makes it possible to restore normal functionality of the von Willebrand factor measured by a VWF:Act/VWF:Ag result>0.7. Advantageously, the mean plasma concentration of von Willebrand factor and the maximum mean plasma concentration of von Willebrand factor are measured after the intravenous administration of the pharmaceutical composition comprising von Willebrand factor according to the invention.

In a particularly advantageous embodiment, the first administration of the pharmaceutical composition comprising von Willebrand factor is carried out before the occurrence of the first haemorrhage or the first bleeding in the patient with the patient's mechanical circulatory support.

Advantageously, the first administration of the pharmaceutical composition comprising von Willebrand factor is carried out four days after the introduction of the patient's mechanical circulatory support.

Advantageously, the first administration of the pharmaceutical composition comprising von Willebrand factor is carried out five days after the introduction of the patient's mechanical circulatory support, preferably six days, preferably seven days after the introduction of the patient's mechanical circulatory support.

Advantageously, the first administration of the pharmaceutical composition comprising von Willebrand factor is carried out between the $4^{th}$ and the $7^{th}$ day after the introduction of the patient's mechanical circulatory support. No first administration is carried out beyond the seventh day. In fact, the administration must be as early as possible in order to observe an effect, confirming that the effectiveness is linked to early blocking of angiogenesis. A later intervention would lead to modulation of the effectiveness.

Advantageously, the first administration of the pharmaceutical composition comprising von Willebrand factor is carried out four to seven days after the introduction of the patient's mechanical circulatory support.

Particularly advantageously, the administration of the pharmaceutical composition comprising von Willebrand factor to the patient with mechanical circulatory support is carried out repeatedly at a rate of two administrations per week.

Advantageously, if the first administration of the von Willebrand factor composition has been carried out on the $4^{th}$ day after the introduction of the patient's mechanical circulatory support, then the second administration of the von Willebrand factor composition is carried out between the $5^{th}$ and the $8^{th}$ day after the introduction of the patient's mechanical circulatory support.

Advantageously, if the first administration of the von Willebrand factor composition has been carried out on the $5^{th}$ day after the introduction of the patient's mechanical circulatory support, then the second administration of the von Willebrand factor composition is carried out between the $6^{th}$ and the $8^{th}$ day after the introduction of the patient's mechanical circulatory support.

Advantageously, if the first administration of the von Willebrand factor composition has been carried out on the $6^{th}$ day after the introduction of the patient's mechanical circulatory support, then the second administration of the von Willebrand factor composition is carried out between the $7^{th}$ and the $8^{th}$ day after the introduction of the patient's mechanical circulatory support.

Advantageously, if the first administration of the von Willebrand factor composition has been carried out on the $7^{th}$ day after the introduction of the patient's mechanical circulatory support, then the second administration of the von Willebrand factor composition is carried out on the $8^{th}$ day after the introduction of the patient's mechanical circulatory support.

Particularly advantageously, the interval between two administrations of the pharmaceutical composition comprising von Willebrand factor according to the invention must not be less than one day, preferably 2 days. Particularly advantageously, the interval between two administrations of the pharmaceutical composition comprising von Willebrand factor according to the invention must not be greater than six days, preferably five days, preferably four days, preferably three days.

Particularly advantageously, the administration of the pharmaceutical composition comprising von Willebrand factor to the patient with mechanical circulatory support is carried out repeatedly at a rate of two administrations per week for at least 15 days.

Advantageously, the administration of the pharmaceutical composition comprising von Willebrand factor to the patient with mechanical circulatory support is carried out repeatedly at a rate of two administrations per week for at least 30 days, preferably 45 days, preferably 60 days, preferably 75 days, preferably 90 days.

In a particularly advantageous embodiment, the pharmaceutical composition comprising von Willebrand factor according to the invention is administered to the patient with mechanical circulatory support repeatedly at a dose of 50 IU/kg of body weight at a rate of two administrations per week for 90 days.

The administration of a von Willebrand factor composition in a preventative manner makes it possible to considerably reduce the risks of the occurrence or the recurrence of a haemorrhage and/or bleeding in these patients. The risks of haemorrhage associated with the introduction of the mechanical circulatory support are preferably reduced by 60%. This preventative administration of von Willebrand factor preferably makes it possible to reduce by more than 70%, preferably 80%, preferably 90% the occurrence of haemorrhage and/or bleeding in these patients. Advantageously, this administration of von Willebrand factor makes it possible to permanently remove any risk of haemorrhage and/or bleeding in the patients with mechanical circulatory support, including the risks of relapse.

Another subject of the invention relates to a method for the preventative treatment of haemorrhage and/or bleeding in patients with mechanical circulatory support, comprising the administration to said patients of a von Willebrand factor composition.

In a particularly advantageous embodiment, the present invention relates to the use of a pharmaceutical composition comprising von Willebrand factor in the manufacture of a medicinal product intended for the prevention of haemorrhage and/or bleeding in patients with mechanical circulatory support.

Another aspect of the invention relates to a pharmaceutical composition comprising von Willebrand factor intended to be used in the treatment of haemorrhage and/or bleeding in patients with mechanical circulatory support.

The inventors have found, surprisingly, that the administration of a dose of at least 30 IU/kg of body weight at the rate of two administrations per week of a pharmaceutical composition comprising von Willebrand factor to patients with mechanical circulatory support enabled the effective treatment of haemorrhage and/or bleeding associated with the introduction of mechanical circulatory support in these patients.

The present invention also relates to a pharmaceutical composition comprising von Willebrand factor intended to be used for the treatment of haemorrhage and/or bleeding in patients with mechanical circulatory support, which comprises the administration to said patients of von Willebrand factor at a dose of at least 30 IU/kg of body weight at the rate of two administrations per week.

The term "treatment" or "curative treatment" is defined as a treatment leading to a cure or a treatment which alleviates, improves and/or eliminates, reduces and/or stabilizes the symptoms of a disease or the suffering that it causes.

Advantageously, the pharmaceutical composition comprising von Willebrand factor according to the invention is administered to the patient at a dose of at least 30 IU/kg of body weight, of at least 40 IU/kg of body weight, preferably 45 IU/kg of body weight, preferably 50 IU/kg of body weight, preferably 55 IU/kg of body weight, preferably 60 IU/kg of body weight, preferably 65 IU/kg of body weight. The dose is preferably 50 IU/kg of body weight.

Advantageously, the dosing regime provides a modification of the multimer distribution of von Willebrand factor with an increase of at least 10%, preferably of at least 15%, advantageously of at least 20% of the multimers larger than 15 mers lasting for 1 hour after the injection. Advantageously, the dosing regime provides a modification of the multimer distribution of von Willebrand factor with an increase of the multimers larger than 15 mers lasting for at least 30 mins. Preferably, the dosing regime provides a modification of the multimer distribution of von Willebrand factor with an increase of the multimers larger than 15 mers lasting for at least 45 mins.

Advantageously, the dosing regime provides a modification of the multimer distribution of von Willebrand factor with an increase of the multimers larger than 15 mers lasting for at least 1 hour after the injection. Advantageously, the dosing regime makes it possible to restore normal functionality of the von Willebrand factor measured by a VWF:Act/VWF:Ag result>0.7.

Advantageously, the mean plasma concentration of von Willebrand factor and the maximum mean plasma concentration of von Willebrand factor are measured after the intravenous administration of the pharmaceutical composition comprising von Willebrand factor according to the invention.

Advantageously, the administration of the pharmaceutical composition comprising von Willebrand factor to the patient with mechanical circulatory support is carried out repeatedly at the rate of two administrations per week for at least 15 days.

Advantageously, the administration of the pharmaceutical composition comprising von Willebrand factor to the patient with mechanical circulatory support is carried out repeatedly at the rate of two administrations per week for at least 30 days, preferably 45 days, preferably 60 days, preferably 75 days, preferably 90 days.

In a particularly advantageous embodiment, the pharmaceutical composition comprising von Willebrand factor according to the invention is administered to the patient with mechanical circulatory support in a curative manner at a dose of 30 IU/kg of body weight repeatedly at the rate of two administrations per week for 90 days.

In an advantageous embodiment, the pharmaceutical composition comprising von Willebrand factor intended to be used in the treatment of haemorrhage and/or bleeding in patients with mechanical circulatory support is depleted of factor VIII. Advantageously, the residual amount of factor VIII in the pharmaceutical composition comprising von Willebrand factor according to the invention is less than or equal to 10 IU/100 IU VWF:RCo.

In an advantageous embodiment, the pharmaceutical composition comprising von Willebrand factor intended to be used in the treatment of haemorrhage and/or bleeding in patients with mechanical circulatory support is depleted of ADAMTS13. Advantageously, the residual amount of ADAMTS13 in the pharmaceutical composition comprising von Willebrand factor is less than or equal to 0.10 ADAMTS13:Act [U/ml].

Another subject of the invention relates to a method for the curative treatment of haemorrhage and/or bleeding in patients with mechanical circulatory support, comprising the administration to said patients of a von Willebrand factor composition.

Advantageously, the method for the curative treatment of haemorrhage and/or bleeding in patients with mechanical circulatory support comprises the administration to said patients of a von Willebrand factor composition, depleted of blood clotting factor VIII.

Advantageously, the method for the curative treatment of haemorrhage and/or bleeding in patients with mechanical circulatory support comprises the administration to said patient of a von Willebrand factor composition at a dose of at least 30 IU/kg of body weight, preferably 40 IU/kg of body weight, preferably 45 IU/kg of body weight, preferably 50 IU/kg of body weight, preferably 55 IU/kg of body weight, preferably 60 IU/kg of body weight, preferably 65 IU/kg of body weight. Particularly advantageously, the dose is 50 IU/kg of body weight.

Advantageously, the method for the curative treatment of haemorrhage and/or bleeding in patients with mechanical circulatory support comprises the administration to said patients of a von Willebrand factor composition repeatedly at the rate of two administrations per week.

Advantageously, the method for the curative treatment of haemorrhage and/or bleeding in patients with mechanical circulatory support comprises the administration to said patient of a von Willebrand factor composition, the first administration of the pharmaceutical composition comprising von Willebrand factor being carried out from the occurrence of the first haemorrhage or the first bleeding in the patient with the patient's mechanical circulatory support.

In a particularly advantageous embodiment, the method for the curative treatment comprising the administration to the patient with mechanical circulatory support of the pharmaceutical composition comprising von Willebrand factor according to the invention at a dose of 50 IU/kg of body weight repeatedly at the rate of two administrations per week for 90 days.

In a particularly advantageous embodiment, the present invention relates to the use of a pharmaceutical composition comprising von Willebrand factor intended to be used in the manufacture of a medicinal product intended for the treatment of haemorrhage and/or bleeding in patients with mechanical circulatory support.

Another aspect, the present invention relates to a process for obtaining the pharmaceutical composition comprising von Willebrand factor. The von Willebrand factor composition can be obtained by processes well known to a person skilled in the art, for example by fractionation of plasma, by expression in cell culture or by expression in the milk of transgenic animals.

According to a particular embodiment, the von Willebrand factor of the invention can be obtained from human blood plasma, either from a fraction of cryoprecipitated human plasma or from the supernatant of cryoprecipitated plasma again containing von Willebrand factor or obtained by conventional fractionation methods (Cohn et al., J. Am. Chem. Soc., 68, 459, 1946 and Kistler et al., Vox Sang., 7, 1962, 414-424), possibly having been subjected to a pre-purification treatment in particular by adsorption on aluminium hydroxide, in which the vWF is complexed to factor VIII. This is then called "plasmatic" von Willebrand factor.

In a particular embodiment, the von Willebrand factor is obtained from a fraction of cryoprecipitated plasma that has been subjected to a prior purification step by chromatography using an anion exchanger of the DEAE-Fractogel®-TSK 650 type, as described in the patents EP 0 359 593 and EP 0 503 991.

According to another particular embodiment, the von Willebrand factor can be obtained by genetic engineering, in particular produced by cells the DNA of which has been modified by genetic recombination in such a way as to express a molecule of FVII, and having the particular characteristics of glycosylation. This is then called recombinant von Willebrand factor. Thus, the von Willebrand factor of the invention is derived from the transcription then the translation of a molecule of DNA coding for the von Willebrand factor in a host cell. The recombinant von Willebrand factor of the invention can be obtained using standard techniques well known to a person skilled in the art, allowing the expression of a protein in a biological system. More particularly, by "recombinant von Willebrand factor" is meant any von Willebrand factor obtained by genetic recombination and expressed by a cultured cell line. The following lines can be mentioned by way of example: BHK (Baby Hamster Kidney) and in particular BHK tk"ts13 (CRL 10314, Waechter and Baserga, Proc. Natl. Acad. Sci. USA 79:1106-1110, 1982), CHO (ATCC CCL 61), COS-I (ATCC CRL 1650), HEK293 (ATCC CRL 1573; Graham et al, J. Gen. Virol. 36:59-72, 1977), Rat Hep I (Rat hepatoma; ATCC CRL 1600), Rat Hep II (Rat hepatoma; ATCC CRL 1548), TCMK (ATCC CCL 139), Human lung (ATCC HB 8065), NCTC 1469 (ATCC CCL 9.1) and DUKX cells (CHO cell line) (Urlaub and Chasin, Proc. Natl. Acad. Sci. USA 77:4216-4220, 1980), 3T3 cells, Namalwa cells, or BHK cells that have been adapted to grow in the absence of serum (document U.S. Pat. No. 6,903,069). Recombinant von Willebrand factor can thus be isolated from a fraction enriched with vWF and/or with factor VIII/recombinant vWF complex isolated from the supernatant of cell cultures according to known techniques.

In another particular embodiment of the invention, the von Willebrand factor is a transgenic von Willebrand factor, i.e. obtained by genetic recombination and expressed by a living tissue, either animal or plant.

Advantageously, the transgenic von Willebrand factor is obtained by genetic recombination and expressed in an animal, called a transgenic animal. By transgenic animal is meant an animal into the genome of which one or more genes has been introduced by transgenesis. Preferably, the von Willebrand factor is in particular produced in the milk of a transgenic animal, the formulation of the invention making it possible to retain a satisfactory level of biological activity of the von Willebrand factor after the lyophilization thereof. According to a preferred embodiment, the human von Willebrand factor is produced in the milk of non-human female transgenic mammals, genetically modified in order to produce this protein. The rabbit, goat, cow, rodent, hamster, camel, llama, Dromedary camel, mouse, rat, pig, sow, horse, dog, cat, ewe, ruminants, hog etc., the list not being limitative, can in particular be mentioned as examples of genetically modified non-human transgenic mammals capable of producing this protein. It is preferably the milk of a transgenic rabbit or goat. The secretion of von Willebrand factor by the mammary glands, making possible the secretion thereof in the milk of the transgenic mammal, implies that the expression of the von Willebrand factor can be controlled in a tissue-dependent manner. Such control methods are well known to a person skilled in the art. The expression is controlled by the sequences allowing the expression of the protein in a particular tissue of the animal. These are, in particular, the WAP promoter sequences, beta casein sequences, beta lactoglobulin sequences and signal peptide sequences. The process for extracting the proteins of interest from the milk of the transgenic animals is described in the patent EP 0 264 166. Transgenic von Willebrand factor can also be isolated from a fraction enriched with vWF and/or with factor VIII/vWF complex obtained from the milk of transgenic mammals as described in the patent U.S. Pat. No. 6,518,482.

Whatever the method of obtaining the von Willebrand factor, from plasma or by genetic engineering (recombinant or transgenic), the von Willebrand factor fraction can be diafiltered in order to incorporate the appropriate excipients intended to allow the von Willebrand factor to be heated to dryness without the risk of denaturation, concentrated by ultrafiltration, packaged in flasks and lyophilized, after a prior addition of an additional pharmaceutically acceptable stabilizer, such as albumin.

Finally, the lyophilizates undergo a final step of viral inactivation by heating the lyophilizate to dryness according to standard conditions, at 80° C. for 72 hours, in order to inactivate the non-enveloped viruses which have not been inactivated and/or eliminated by at least one of the two preceding steps for the inactivation and/or elimination of viruses. The lyophilizates heated to dryness are then reconstituted in an aqueous medium compatible with clinical use, preferably in 10 ml of water for injection (WFI) in order to obtain an injectable formulation.

The injectable formulation can be administered parenterally, preferably by intravenous, sub-cutaneous or intramuscular route. The administration of the liquid form (solution or suspension, before drying) or the powder form, by any appropriate route or means, is not excluded. In a particular embodiment of the invention, the injectable formulation is administered intravenously.

EXAMPLES

Example 1: Preparation of a Von Willebrand Factor Composition

1) Obtaining a Fraction Containing vWF

A cryoprecipitate of human plasma is used, resuspended in an aqueous heparin sodium solution (2 U/ml), at a pH of 7-7.1.

This cryoprecipitate solution is subjected to a pre-purification on aluminium hydroxide in order to eliminate the main contaminants, as described in the patent EP 0 359 593. The pre-purified supernatant is then recovered and is subjected to a standard viral inactivation treatment by solvent-detergent, in the presence of Tween®-TNBP.

The pre-purified cryoprecipitate solution is then injected into a Fractogel® TSK-DEAE 650 (M) type chromatography column with a length of 25 cm and a diameter of 1 cm, equilibrated beforehand with a buffer constituted by 0.01 M trisodium citrate, 0.001 M calcium chloride, 0.11 M sodium chloride, 0.12 M glycine and 0.016 M lysine, adjusted to a pH of 7.01, the linear velocity of the mobile phase of which is set at 100 cm/hour. The von Willebrand factor, the factor VIII and the fibronectin are retained on the chromatographic support. The weakly-retained proteins or those not retained by the support, principally the fibrinogen and the immunoglobulin Gs (IgGs), are eliminated in the filtrate, as well as the Tween® and TNBP, by several successive washings with the same buffer.

The protein content is monitored by measuring the absorption at 280 nm (labelled O.D. below).

When the O.D., measured at 280 nm, has returned to the baseline, the concentration of sodium chloride in the buffer is increased to 0.15 M. Under these conditions, the von Willebrand factor is eluted. The eluate thus obtained is very rich in von Willebrand factor and in fibronectin and also contains Tween® and TNBP, as well as residual factor VIII.

2) Chromatographic Separation

The previously-eluted fraction enriched with von Willebrand factor, constituting one batch of starting fraction containing the von Willebrand factor according to the invention, is loaded into a DEAE-Fractogel®-TSK 650 (M) type chromatography column with a length of 25 cm and a diameter of 1 cm, equilibrated beforehand with the same buffer as that in 1), the osmolarity of which is 387 mosmolkg$^{-1}$, the linear velocity of which is set at 100 cm/hour.

140 ml of this fraction containing 12.9 IU vWF/ml and 6.6 IU factor VIII/ml, or an R ratio of 51.1% (R=FVIII:C/FvW: RCo) is injected.

The column is then washed with an acidic buffer of 20 mM sodium acetate, adjusted to a pH of 4.35 and 80 mosmolkg$^{-1}$, with a linear velocity of 150 cm/hour. Under these conditions, a very good elimination not only of the viral inactivation agent residues but also of the fibronectin and above all of factor VIII which was again complexed to the von Willebrand factor is ensured, without precipitation of these proteins being observed in the column. When the O.D. has returned to the baseline, the linear velocity is brought back to 100 cm/hour then the column is rinsed and equilibrated with the same buffer as previously, containing NaCl at 0.11 M.

The fraction containing the von Willebrand factor is eluted by increasing the concentration of the NaCl of the equilibrating buffer to 0.17 M, adjusting to a pH of 6.95 and 492 mosmolkg$^{-1}$.

The eluted von Willebrand factor fraction then undergoes standard sterilizing filtration treatments on filters of 0.22 µm, nanofiltration on filters of 35 nm, diafiltration and ultrafiltration according to known techniques so that the von Willebrand factor concentrate has a specific activity (S.A.) of at least 90 IU RCo/mg of protein.

Albumin at 10 g/l is added to the von Willebrand factor concentrates thus obtained then it is lyophilized at −40° C. for 48 hours. The lyophilization is followed by a heat viral inactivation treatment by heating the lyophilizate to dryness at 80° C. for 72 hours.

Example 2: Effect of the Administration of a Von Willebrand Factor Composition on the Prevention of Haemorrhage and/or Bleeding in Patients with Mechanical Circulatory Support The present study is based on 136 patients over the age of 18 and requiring the introduction of mechanical circulatory support due to advanced heart failure.

In the following, the abbreviation d means "day". The abbreviation d=0 corresponds to the day of surgery, thus-named day 0. By way of example, the abbreviation d+4 corresponds to the 4th day after surgery.

On d=0 the patients have the mechanical circulatory support device implanted through the implantation of a HeartMate II continuous flow pump. Between d+4 and d+7 the patients received a first administration of the pharmaceutical composition comprising von Willebrand factor according to the invention at a dose of 50 IU/kg of body weight. The administration of this pharmaceutical composition comprising von Willebrand factor was carried out at the rate of two administrations per week and at a dose of 50 IU/kg of body weight for 90 days.

The occurrence of haemorrhage and/or bleeding was monitored for each of the patients for 90 days. In addition, the development of the angiogenic markers (VEGF, angiopoietin 2, galectin 1 and 3) as well as the development of the pharmacological characteristics of the von Willebrand factor (development of the vWF:Act, vWF:Ag, vWF:CBA ratios and the levels of high-molecular weight (HMW) multimers were monitored at d+15, d+30, d+45, d+60, d+75 and d+90.

The results show that the administration of 50 IU/kg of the von Willebrand factor composition according to the invention at the rate of two administrations per week for 90 days makes it possible to prevent the occurrence of haemorrhage and/or bleeding in these patients.

The invention claimed is:

1. A method of treating or preventing haemorrhage and/or bleeding in patients with mechanical circulatory support, comprising administering to the patient a pharmaceutical composition comprising von Willebrand factor in an amount effective for treating or preventing haemorrhage and/or bleeding in patients with mechanical circulatory support, wherein the composition contains a residual amount of factor VIII less than or equal to 10 IU/100 IU VWF:RCo, and wherein the composition is administered to the patient at a dose of 45 IU/kg to 55 IU/kg of body weight.

2. The method according to claim 1, wherein the dose is 50 IU/kg of body weight.

3. The method according to claim 1, wherein the dose is administered repeatedly at a rate of two administrations per week.

4. The method according to claim 1, wherein the pharmaceutical composition is first administered four to seven days after the mechanical circulatory support is introduced into the patient.

5. The method according to claim 1, wherein the composition is administered intravenously.

6. The method according to claim 1, wherein the composition is depleted of factor VIII.

7. The method according to claim 1, wherein the composition is depleted of ADAMTS 13.

8. The method according to claim 1, wherein high-molecular weight multimers represent at least 65% of total multimer content of von Willebrand factor contained in the pharmaceutical composition.

9. The method according to claim 1, wherein high-molecular weight multimers represent at least 70% of total multimer content of von Willebrand factor contained in the pharmaceutical composition.

10. The method according to claim 1, wherein high-molecular weight multimers represent at least 75% of total multimer content of von Willebrand factor contained in the pharmaceutical composition.

11. The method according to claim 1, wherein the content of high-molecular weight multimers is close to that of plasma.

12. The method according to claim 1, wherein the high-molecular weight multimers are present in amounts sufficient for vivo activity.

* * * * *